United States Patent [19]

Patel

[11] Patent Number: 5,879,929
[45] Date of Patent: Mar. 9, 1999

[54] ENZYMATIC PROCESSES FOR THE RESOLUTION OF ENANTIOMERIC MIXTURES OF LACTAMS USEFUL AS INTERMEDIATES IN THE PREPARATION OF TAXANES

[75] Inventor: Ramesh N. Patel, Bridgewater, N.J.

[73] Assignee: Bristol-Myers Squibb Company, Princeton, N.J.

[21] Appl. No.: 461,236

[22] Filed: Jun. 5, 1995

Related U.S. Application Data

[63] Continuation of Ser. No. 92,170, Jul. 14, 1993, abandoned.
[51] Int. Cl.$^6$ ............................... C07C 1/04; C07F 1/04
[52] U.S. Cl. ..................... 435/280; 435/874; 435/921; 435/939; 435/123
[58] Field of Search ................................ 435/280, 123

[56] References Cited

U.S. PATENT DOCUMENTS

| | | | |
|---|---|---|---|
| 4,492,757 | 1/1985 | Kato et al. | 435/280 |
| 4,943,528 | 7/1990 | Nakamura et al. | 435/158 |
| 5,015,744 | 5/1991 | Holton et al. | 549/510 |
| 5,254,580 | 10/1993 | Chen et al. | 514/449 |
| 5,272,171 | 12/1993 | Ueda et al. | 514/449 |
| 5,294,637 | 3/1994 | Chen et al. | 514/449 |
| 5,294,737 | 3/1994 | Ojima | 562/444 |
| 5,300,638 | 4/1994 | Farina et al. | 540/357 |
| 5,567,614 | 10/1996 | Patel et al. | 435/280 |

FOREIGN PATENT DOCUMENTS

| | | |
|---|---|---|
| 9213106 | 10/1992 | Australia . |
| 336841 | 10/1989 | European Pat. Off. . |
| 400971 | 12/1990 | European Pat. Off. . |
| 404586 | 12/1990 | European Pat. Off. . |
| 405104 | 1/1991 | European Pat. Off. . |
| 414610 | 2/1991 | European Pat. Off. . |
| 421283 | 4/1991 | European Pat. Off. . |
| 428376 | 5/1991 | European Pat. Off. . |
| 529483 | 3/1993 | European Pat. Off. . |
| 534707 | 3/1993 | European Pat. Off. . |
| 534708 | 3/1993 | European Pat. Off. . |
| 534709 | 3/1993 | European Pat. Off. . |
| 552041 | 7/1993 | European Pat. Off. . |
| 558959 | 9/1993 | European Pat. Off. . |
| 582469 | 2/1994 | European Pat. Off. . |
| 604910 | 7/1994 | European Pat. Off. . |
| WO 90/14434 | 11/1990 | WIPO . |
| WO 91/00923 | 1/1991 | WIPO . |

OTHER PUBLICATIONS

Nagai et al., Chem. Pharm. Bull. 40(8) 2227–2229 (Aug. 1992).
Brieva R et al, J. Org. Chem. 58:1068–1075 (1993).
Okumura S et al, BBA 575:156–165 (1979).
Hills M et al, BBA 1042:237–240 (1990).
Jones JB, Tetrahedron 42:3351–3403 (1986).
Abdel–Magid et al., "Metal–Assisted Aldol Condensation of Chiral α–Halogenated Imide Enolates: A Stereocontrolled Chiral Epoxide Synthesis," *J. Am. Chem. Soc.*, 108, pp. 4595–4602 (1986).
Barton et al., "Asymmetric Synthesis of 1,3,4–Trisubstituted and 3,4–Disubstituted 2–Azetidinones: Stragegy Based on the Use of D–Glucosamine as a Chiral Auxiliary in the Staudinger Reaction," *J. Chem. Soc. Perkin Trans I*, pp. 3211–3212 (1990).
Borer et al., "An Asymmetric Synthesis of a 3–Hydroxy–β–Lactam by Ketene–Imine Cycloaddition: Utilization of Chiral Ketenes from Carbohydrates," *Tetrahedron Letters*, pp. 1039–1040 (1991).
Chemical Abstracts, vol. 105, No. 3, 21 Jul. 1986, abstract No. 23102k, p. 537 (JP–A–60 248 192; 7 Dec. 1985).
Cooper et al., "Chiral control of the Staudinger reaction," *Pure & Appl. Chem.*, 59, No. 3, pp. 485–492 (1987).
Denis et al., "An Efficient, Enentioselective Synthesis of the Taxol Side Chain," *J. Org. Chem.*, 51 pp. 46–50 (1986).
Denis et al., "An Improved Synthesis of the Taxol Side Chain and of RP 56976", *J. Org. Chem.*, 55, pp. 1957–1959 (1990).
Dordick, *Biotechnol. Prog.*, 8:259–67 (1992).
Fones, "The Isomers of the β–Phenylserines", *J. Biol. Chem.*, 204, pp. 323–328 (1953).
Georg et al., "Stereoselective Syn Aldol Reaction of the Lithium Ester Enolate of Ethyl N,N–Dimethylglycine in the Presence of Triethylborane", *Tetrahedron Letters*, 32, No. 40, pp. 5521–5524 (1991).
Georg et al., "Asymmetric Synthesis of β–Lactams and N–Benzoyl–3–Phenylisoserines via the Staudinger Reaction", *Tetrahedron Letters*, 32, No. 27, pp. 3151–3154 (1991), plus Correction (1 page).
Georg et al., "An Improved Method for the Stereoselective Synthesis of β–Lactams from Carboxylic Acids and Imines", *Tetrahedron Letters*, 32, No. 5, pp. 581–584 (1991).
Gou et al., *J. Org. Chem.*, 58, 1287–1289 (1993).
Honig et al., "Chemo–Enzymatic Synthesis of All Isomeric 3–Phenylserines and –Isoserines", *Tetrahedron*, 46, No. 11, pp. 3841–3850 (1990).
Chemical Abstracts, vol. 115, No. 17, 28 Oct. 1991, abstract No. 183831g, Hoenig, H., "Chemoenzymic syntheses of enantiomerically pure hydroxy amino acids", p. 985; AND complete article: Chem. Biol. Med. (Pap. Int. Congr. Amino Acids Res.), pp. 134–142 (1990).
Iriuchijima et al., *Agric. Biol. Chem.*, 45:1389–92 (1981).
Kato et al., *Tetrahedron Letters*, 28:1303–1306 (1987).
Langrand et al., "Lipase Catalyzed Reactions and Strategy for Alcohol Resolution", *Tetrahedron Letters*, vol. 27, No. 1, pp. 29–32 (1986).

(List continued on next page.)

Primary Examiner—Sandra E. Saucier
Attorney, Agent, or Firm—Suzanne E. Babjko; Frank P. Hoffman

[57] ABSTRACT

Methods for the enzymatic resolution of mixtures of enantiomers, such as β-lactam compounds, which may be employed as intermediates in the preparation of taxanes bearing a C-13 sidechain containing a heterocyclic or cycloalkyl group, the latter useful in the pharmaceutical field.

32 Claims, No Drawings

OTHER PUBLICATIONS

Ojima et al., "Efficient and Practical Asymmetric Synthesis of the Taxol C-13 Side Chain, N-Benzoyl-(2R, 3S)-3-phenylisoserine, and Its Analogues via Chiral 3-Hydroxy-4-aryl-β-lactams through Chiral Ester Enolate-Imine Cyclocondensation", *J. Org. Chem.,* 56 pp. 1681–1683 (1991).

Ojima et al., *Tetrahedron,* vol. 48, No. 34, pp. 6985–7012 (1992).

Ojima et al., *Tetrahedron Lett.,* vol. 33, No. 39, pp. 5737–5740 (1992).

Palomo et al., "Highly Stereoselective Synthesis of α-Hydroxy-β-Amino acids through β-Lactams: Application to the Synthesis of the Taxol and Bestatin Side Chains and Related Systems", *Tetrahedron Letters,* vol. 31, No. 44, pp. 6429–6432 (1990).

Parida et al., *J. Am. Chem. Soc.,* 113:2253–59 (1991).

Sonnet et al., *Lipids,* 26: 295–300 (1991).

Yamazaki et al., *Bioorg. & Med. Chem. Lett.,* 1:271–6 (1991).

ENZYMATIC PROCESSES FOR THE RESOLUTION OF ENANTIOMERIC MIXTURES OF LACTAMS USEFUL AS INTERMEDIATES IN THE PREPARATION OF TAXANES

This is a continuation of application Ser. No. 08/092,170 filed on Jul. 14, 1993 now abandoned.

FIELD OF THE INVENTION

The present invention relates to enzymatic processes for the resolution of enantiomeric mixtures of compounds useful as intermediates in the preparation of taxanes, particularly for the preparation of taxanes bearing a C-13 sidechain containing a heterocyclic or cycloalkyl group.

BACKGROUND OF THE INVENTION

Taxanes are diterpene compounds which find utility in the pharmaceutical field. For example, taxol analogues containing heterocyclic or cycloalkyl groups on the C-13 sidechain find utility as anticancer agents. Such taxol analogues may be prepared through semi-synthetic routes, particularly by the coupling of β-lactam or open chain intermediates to the taxane core to form a sidechain at C-13. As the stereochemistry of these analogues may affect their pharmaceutical activity, methods allowing efficient stereospecific preparation of the intermediate β-lactam and open chain compounds, as well as the final taxane products, are sought in the art.

SUMMARY OF THE INVENTION

The present invention provides efficient methods for the resolution of enantiomeric mixtures, preferably racemic mixtures, of compounds useful as intermediates in the preparation of taxanes bearing a C-13 sidechain containing a heterocyclic or cycloalkyl group, and thus for the stereospecific preparation of these compounds.

Specifically, the present invention provides a method for the resolution of a mixture I comprising the enantiomers Ia and Ib, where $R^1$ is in the cis position relative to $R^2$ in both Ia and Ib, or where $R^1$ is in the trans position relative to $R^2$ in both Ia and Ib:

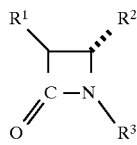
(Ia)

and

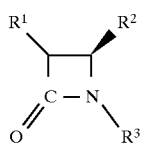
(Ib)

where
$R^1$ is hydroxyl; halo; or —O—C(O)—$R^4$, where
$R^4$ is alkyl, alkenyl, alkynyl, aryl, cycloalkyl, cycloalkenyl or heterocyclo;
$R^2$ is heterocyclo or cycloalkyl; and
$R^3$ is hydrogen; $R^4$; —C(O)—O$R^4$; or —C(O)—$R^4$, where $R^4$ is independently selected from those groups recited for $R^4$ above;
comprising the step of contacting said mixture I with an enzyme or microorganism capable of catalyzing the stereoselective conversion of one of said compounds Ia or Ib to a non-enantiomeric form, and effecting said conversion.

The present invention also provides a process for the resolution of a mixture IV comprising the enantiomers IVa and IVb:

$$R^2-T^a-C(O)-OR^6 \qquad (IVa)$$

and $$R^2-T^b-C(O)-OR^6 \qquad (IVb)$$

where
$T^a$ is

and $T^b$ is

or
$T^a$ is

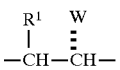

and $T^b$ is

where $R^1$ is in the erythro position relative to the group W in both IVa and IVb, or where $R^1$ is in the threo position relative to the group W in both IVa and IVb;
W is —NH$R^3$ or —N$_3$;
$R^1$ is hydroxyl; halo; or —O—C(O)—$R^4$, where
$R^4$ is alkyl, alkenyl, alkynyl, aryl, cycloalkyl, cycloalkenyl or heterocyclo;
$R^2$ is heterocyclo or cycloalkyl;
$R^3$ is hydrogen; $R^4$; —C(O)—O$R^4$; or —C(O)—$R^4$, where $R^4$ is independently selected from those groups recited for $R^4$ above; and
$R^6$ is hydrogen; or $R^4$, where $R^4$ is independently selected from those groups recited for $R^4$ above;
comprising the step of contacting said mixture IV with an enzyme or microorganism capable of catalyzing the stereoselective conversion of one of said compounds IVa or IVb to a non-enantiomeric form, and effecting said conversion.

Exemplary embodiments for the aforementioned stereoselective conversions include stereoselective hydrolysis, stereoselective esterification, stereoselective transesterification and stereoselective dehalogenation, particularly stereoselective hydrolysis or esterification.

Groups, such as hydroxyl groups, on the compounds of formulae I or IV may optionally be protected for use in the resolution methods of the present invention; such groups may optionally be subsequently deprotected.

DETAILED DESCRIPTION OF THE INVENTION

The methods of the present invention are described further as follows.

C is Enantiomers

The following pair of cis enantiomers may be separated by the enzymatic methods of the instant invention:

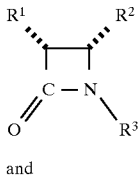
(Ia(1))

and

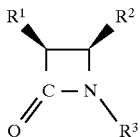
(Ib(1))

that is, enantiomers Ia and Ib where $R^1$ is in the cis position relative to $R^2$ in both Ia and Ib.

It is preferred to resolve a mixture of cis enantiomers as described above according to the methods of the instant invention.

Trans Enantiomers

The following pair of trans enantiomers may be separated by the enzymatic methods of the instant invention:

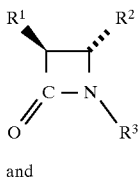
(Ia(2))

and

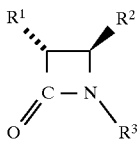
(Ib(2))

that is, enantiomers Ia and Ib where $R^1$ is in the trans position relative to $R^2$ in both Ia and Ib.

Erythro Enantiomers

The following pairs of erythro enantiomers may be separated by the enzymatic methods of the instant invention:

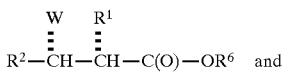
(IVa(1))

and

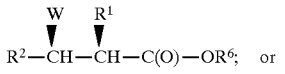
(IVb(1)); or

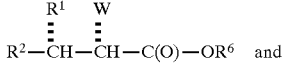
(IVa(2))

and (IVb(2))

$$R^2-\overset{R^1}{\underset{\vdots}{CH}}-\overset{W}{\underset{\vdots}{CH}}-C(O)-OR^6;$$

that is, enantiomers IVa and IVb where $R^1$ is in the erythro position relative to the group W in both IVa and IVb.

Threo Enantiomers

The following pairs of threo enantiomers may be separated by the enzymatic methods of the instant invention:

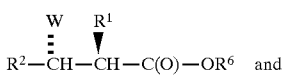
(IVa(3))

and $$R^2-\overset{W}{\underset{\vdots}{CH}}-\overset{R^1}{\underset{\vdots}{CH}}-C(O)-OR^6; \quad \text{or} \quad (IVb(3))$$

$$R^2-\overset{R^1}{\underset{\vdots}{CH}}-\overset{W}{\underset{\vdots}{CH}}-C(O)-OR^6 \quad \text{and} \quad (IVa(4))$$

$$R^2-\overset{R^1}{\underset{\vdots}{CH}}-\overset{W}{\underset{\vdots}{CH}}-C(O)-OR^6 \quad (IVb(4))$$

that is, enantiomers IVa and IVb where $R^1$ is in the threo position relative to the group W in both IVa and IVb.

Preferred Methods for the Resolution of Mixture I

Mixture I, comprising an enantiomeric mixture of β-lactams Ia and Ib, is preferably resolved by stereoselective hydrolysis, esterification or dehalogenation. A particularly preferred method for the resolution of a mixture I comprising the enantiomers Ia(1) and Ib(1):

(Ia(1))

and

(Ib(1))

to form a mixture II comprising the compounds IIa(1) and IIb(1):

(IIa(1))

and

(IIb(1))

where $R^2$ is heterocyclo or cycloalkyl; and $R^3$ is hydrogen; $R^4$; —C(O)—OR$^4$; or —C(O)—R$^4$,
where $R^4$ is alkyl, alkenyl, alkynyl, aryl, cycloalkyl, cycloalkenyl or heterocyclo;

comprises one of the following steps (i), (ii), or (iii):

(i) where
$R^1$ is —O—C(O)—R$^4$, where $R^4$ is independently selected from those groups recited for $R^4$ above; and one of $R^{1a}$ or $R^{1b}$ is the same as $R^1$ and the other of $R^{1a}$ or $R^{1b}$ is hydroxyl;

the step of contacting said mixture I, in the presence of water and/or an organic alcohol, with an enzyme or microorganism capable of catalyzing the stereoselective hydrolysis of mixture I to provide said mixture II; or (ii) where
$R^1$ is hydroxyl; and
one of $R^{1a}$ or $R^{1b}$ is hydroxyl and the other of $R^{1a}$ or $R^{1b}$ is $R^4$—C(O)—O—, where $R^4$ is independently selected from those groups recited for $R^4$ above;

the step of contacting said mixture I, in the presence of a compound III:

$R^4$—C(O)—L (III)

where $R^4$ is as defined above for $R^{1a}$ or $R^{1b}$ and L is a leaving group, with an enzyme or microorganism capable of catalyzing the stereoselective esterification of mixture I to provide said mixture II; or (iii) where
$R^1$ is a halogen atom; and
one of $R^{1a}$ or $R^{1b}$ is halogen and the other of $R^{1a}$ or $R^{1b}$ is hydroxyl;
the step of contacting said mixture I, in the presence of a hydroxide ion donor, with an enzyme or microorganism capable of catalyzing the stereoselective dehalogenation of mixture I to provide said mixture II.

The above methods may be employed in the resolution of other enantiomeric mixtures of the instant invention, although resolution of the above cis enantiomers Ia(1) and Ib(1) is preferred.

Preferred Methods for the Resolution of Mixture IV

Mixture IV is preferably resolved by stereoselective hydrolysis, esterification, dehalogenation or transesterification. A particularly preferred method for the resolution of a mixture IV comprising the enantiamers IVa(1) and IVb(1):

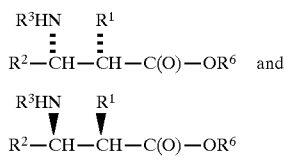
and
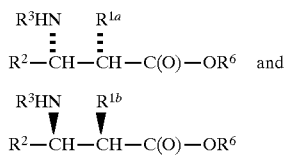

to form a mixture V comprising compounds Va(1) and Vb(1):

$$\begin{array}{c} R^3HN \quad R^{1a} \\ \vdots \quad \vdots \\ R^2—CH—CH—C(O)—OR^6 \end{array} \quad (Va(1))$$
and
$$\begin{array}{c} R^3HN \quad R^{1b} \\ \blacktriangledown \quad \blacktriangledown \\ R^2—CH—CH—C(O)—OR^6 \end{array} \quad (Vb(1))$$

where
$R^2$ is heterocyclo or cycloalkyl;
$R^3$ is hydrogen; $R^4$; —C(O)—$OR^4$; or —C(O)—$R^4$, where $R^4$ is alkyl, alkenyl, alkynyl, aryl, cycloalkyl, cycloalkenyl or heterocyclo; and
$R^6$ is hydrogen; or $R^4$, where $R^4$ is independently selected from those groups recited for $R^4$ above;
comprises one of the following steps (i), (ii), or (iii):
(i) where
$R^1$ is —O—C(O)—$R^4$, where $R^4$ is independently selected from those groups recited for $R^4$ above; and one of $R^{1a}$ or $R^{1b}$ is the same as $R^1$ and the other of $R^{1a}$ or $R^{1b}$ is hydroxyl;
the step of contacting said mixture IV, in the presence of water and/or an organic alcohol, with an enzyme or microorganism capable of catalyzing the stereoselective hydrolysis of mixture IV to provide said mixture V; or
(ii) where
$R^1$ is hydroxyl; and
one of $R^{1a}$ or $R^{1b}$ is hydroxyl and the other of $R^{1a}$ or $R^{1b}$ is $R^4$—C(O)—O—, where $R^4$ is independently selected from those groups recited for $R^4$ above;
the step of contacting said mixture IV, in the presence of a compound III:

$R^4$—C(O)—L (III)

where $R^4$ is as defined above for $R^{1a}$ or $R^{1b}$ and L is a leaving group, with an enzyme or microorganism capable of catalyzing the stereoselective esterification of mixture IV to provide said mixture V; or (iii) where
$R^1$ is a halogen atom; and
one of $R^{1a}$ or $R^{1b}$ is halogen and the other of $R^{1a}$ or $R^{1b}$ is hydroxyl;
the step of contacting said mixture IV, in the presence of a hydroxide ion donor, with an enzyme or microorganism capable of catalyzing the stereoselective dehalogenation of mixture IV to provide said mixture V.

A further particularly preferred method for the resolution of a mixture IV comprising the enantiomers IVa(1) and IVb(1):

and

to form a mixture VI comprising compounds VIa(1) and VIb(1):

and

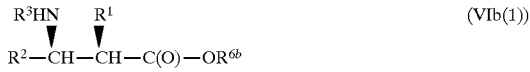

where
$R^1$ is hydroxyl; halo; or —O—C(O)—$R^4$, where $R^4$ is alkyl, alkenyl, alkynyl, aryl, cycloalkyl, cyloalkenyl or heterocyclo;
$R^2$ is heterocyclo or cycloalkyl; and
$R^3$ is hydrogen; $R^4$; —C(O)—$OR^4$; or —C(O)—$R^4$, where $R^4$ is independently selected from those groups recited for $R^4$ above;
comprises one of the following steps (i), (ii), or (iii):
(i) where
$R^6$ is hydrogen; and
one of $R^{6a}$ or $R^{6b}$ is hydrogen and the other of $R^{6a}$ or $R^{6b}$ is $R^4$, where $R^4$ is independently selected from those groups recited for $R^4$ above;
the step of contacting said mixture IV, in the presence of an organic alcohol of the formula VII:

$R^4$—OH (VII)

where $R^4$ is as defined above for $R^{6a}$ or $R^{6b}$, with an enzyme or microorganism capable of catalyzing the stereoselective esterification of mixture IV to provide said mixture VI; or (ii) where
$R^6$ is $R^4$, where $R^4$ is independently selected from those groups recited for $R^4$ above; and
one of $R^{6a}$ or $R^{6b}$ is the same as $R^6$ and the other of $R^{6a}$ or $R^{6b}$ is hydrogen;
the step of contacting said mixture IV, in the presence of water, with an enzyme or microorganism capable of catalyzing the stereoselective hydrolysis of mixture IV to provide said mixture VI; or (iii) where R⁶ is R⁴, where R⁴ is independently selected from those groups recited for R⁴ above; and one of R^{6a} or R^{6b} is the same as R⁶ and the other of R^{6a} or R^{6b} is R⁷, where R⁷ is alkyl, alkenyl, alkynyl, aryl, cycloalkyl, cycloalkenyl or heterocyclo, except that R⁷ is not the same as R⁶;

the step of contacting said mixture IV, in the presence of an organic alcohol of the formula VIII:

R⁷—OH  (VIII)

where R⁷ is as defined above, with an enzyme or microorganism capable of catalyzing the stereoselective transesterification of mixture IV to provide said mixture VI.

The above methods may be employed in the resolution of other enantiomeric mixtures of the instant invention, although resolution of the above enantiomers IVa(1) and IVb(1) is preferred.

The compound pairs so prepared, such as IIa(1) and IIb(1), are non-enantiomeric and may subsequently be separated to yield optically active, preferably optically pure, compounds. An optical purity greater than 99%, particularly 99.5%, is preferred.

The instant invention also provides a compound of the mixture I or IV substantially free of other isomers, which compound may be prepared by the methods of the invention.

Definitions

The term "stereoselective conversion", as used herein, refers to the preferential reaction of one enantiomer relative to another, that is, asymmetric, enantioselective, reaction. Likewise, the terms "stereoselective hydrolysis", "stereoselective esterification", stereoselective dehalogenation" and "stereoselective transesterification" refer to the preferential hydrolysis, esterification, dehalogenation and transesterification, respectively, of one enantiomer relative to another.

The term "mixture", as said term is used herein in relation to enantiomeric compounds, denotes mixtures having equal (racemic) or non-equal amounts of enantiomers.

The term "resolution" as used herein denotes partial, as well as, preferably, complete resolution.

The term "non-enantiomeric form" as used herein denotes the structure of a compound, originally one of an enantiomeric pair, in which at least one group has been modified so that said compound is no longer the mirror image of the other compound of the original enantiomeric pair.

The terms "enzymatic process" or "enzymatic method" as used herein denote a process or method of the present invention employing an enzyme or microorganism.

The terms "alkyl", "alkan" or "alk" as employed herein alone or as part of another group denote both straight and branched chain, optionally substituted hydrocarbons groups containing 1 to 15 carbons in the normal chain, preferably 1 to 6 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Exemplary substituents include one or more groups selected from the following: halo (especially chloro), trihalomethyl, alkoxy (for example, where two alkoxy substituents form an acetal), aryl such as unsubstituted aryl, alkyl-aryl or haloaryl, cycloalkyl such as unsubstituted cycloalkyl or alkyl-cycloalkyl, hydroxy or protected hydroxy, carboxyl, alkyloxycarbonyl, alkylamino, alkylcarbonylamino, amino, arylcarbonylamino, nitro, cyano, thiol or alkylthio.

The term "alkenyl" as employed herein alone or as part of another group denotes such optionally substituted groups as described above for alkyl, further containing at least one carbon to carbon double bond. Exemplary substituents include one or more alkyl groups as described above, and/or one or more groups described above as alkyl substituents.

The term "alkynyl" as employed herein alone or as part of another group denotes such optionally substituted groups described above for alkyl, further containing at least one carbon to carbon triple bond. Exemplary substituents include one or more alkyl groups as described above, and/or one or more groups described above as alkyl substituents.

The term "cycloalkyl" as employed herein alone or as part of another group denotes optionally substituted saturated cyclic hydrocarbon groups containing one to three rings and 3 to 12 ring carbons, preferably 3 to 8 ring carbons, such as cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, and/or one or more groups described above as alkyl substituents.

The term "cycloalkenyl" as employed herein alone or as part of another group denotes such optionally substituted groups as described above for cycloalkyl, further containing at least one carbon to carbon double bond in the ring system. Exemplary substituents include one or more alkyl groups as described above, and/or one or more groups described above as alkyl substituents.

The terms "aryl" or "ar" as employed herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Exemplary substituents (preferably three or fewer) include one or more of the following groups: alkyl such as unsubstituted alkyl, haloalkyl, or cycloalkyl-alkyl, halogen, alkoxy such as unsubstituted alkoxy or haloalkoxy, hydroxy, aryloxy such as phenoxy, R⁴-carbonyloxy, where R⁴ is as defined above, allyl, cycloalkyl, alkylamino, dialkylamino, amido such as alkylcarbonylamino or arylcarbonylamino, amino, nitro, cyano, alkenyl, thiol, R⁴-carbonyl, where R⁴ is as defined above, or methylenedioxy where the methylene group may be substituted by 1 or 2 lower alkyl groups, 1 or 2 arylalkenyl groups, and/or 1 or 2 alkylthio groups. Particularly preferred aryl groups are phenyl and substituted phenyl, especially phenyl substituted by one or more hydroxyl, alkyl and/or alkoxy groups.

The terms "halogen" or "halo" as used herein alone or as part of another group refer to chlorine, bromine, fluorine, and iodine.

The terms "heterocyclo" or "heterocyclic" as used herein alone or as part of another group denote optionally substituted fully saturated or unsaturated, monocyclic or bicyclic, aromatic or nonaromatic hydrocarbon groups having at least one heteroatom in at least one ring, and preferably 5 or 6 atoms in each ring. The heterocyclo group preferably has 1 or 2 oxygen atoms, 1 or 2 sulfur atoms, and/or 1 to 4 nitrogen atoms in the ring, and may be bonded to the remainder of the molecule through a carbon or heteroatom. Exemplary substituents include one or more of the following groups:

halogen, alkoxy, hydroxy, aryl such as phenyl or halophenyl, alkanoyloxy, arylcarbonyloxy such as benzoyloxy, alkyl such as aralkyl, alkylamino, alkanoylamino, arylcarbonylamino, amino, nitro, cyano, and thiol. Exemplary heterocyclo groups include thienyl, furyl, pyrrolyl, pyridyl; imidazolyl, pyrrolidinyl, piperidinyl, azepinyl, indolyl, isoindolyl, quinolinyl, isoquinolinyl, benzothiazolyl, benzoxazolyl, benzimidazolyl, benzoxadiazolyl, and benzofurazanyl.

The term "hydroxyl protecting group" as used herein denotes a group capable of protecting a free hydroxyl group ("protected hydroxyl") which, subsequent to the reaction for which protection is employed, may be removed without disturbing the remainder of the molecule. A variety of protecting groups for the hydroxyl group and the synthesis thereof may be found in "Protective Groups in Organic Synthesis" by T. W. Greene, John Wiley and Sons, 1981, or Fiser & Fiser. Exemplary hydroxyl protecting groups include methoxymethyl, 1-ethoxyethyl, benzyloxymethyl, (β-trimethylsilylethoxy)methyl, tetrahydropyranyl, 2,2,2-trichloroethoxycarbonyl, t-butyl(diphenyl)silyl, trialkylsilyl, trichloromethoxycarbonyl and 2,2,2-trichloroethoxymethyl.

Starting Materials

The starting materials for the present resolution methods may be obtained as described in the Examples herein, or by methods analogous to those described in U.S. patent application Ser. No. 07/822,015, filed Jan. 15, 1992.

The starting mixtures I or IV may contain, for example, the diastereomers of the compounds Ia and Ib or IVa and IVb, although it is preferred that such compounds are separated prior to conducting the enzymatic resolution methods of the present invention.

Preferred Compounds

Cis compounds of the formula I have a stereoisomeric configuration which is preferred in compounds employed as intermediates in the preparation of C-13 sidechain-bearing taxanes. Compounds of the mixtures I and II having the same absolute stereoconfiguration corresponding to that of a compound Ia where $R^1$ is acetyloxy, $R^2$ is furyl and $R^3$ is hydrogen in the 3R,4S configuration are particularly preferred.

Erythro compounds of the formula IV have a stereoisomeric configuration which is preferred in compounds employed as intermediates in the preparation of C-13 sidechain-bearing taxanes. Compounds of the mixtures IV, V and VI having the same absolute stereoconfiguration corresponding to that of a compound IVa(1) where $R^1$ is hydroxyl, $R^2$ is furyl, W is —$NHR^3$ and $R^3$ is hydrogen, and $R^6$ is hydrogen in the 2R,3S configuration are preferred. In mixture IV, $T^a =$

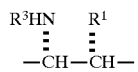

and $T^b =$

is preferred.

Resolution of β-lactams of the formula I is preferred.

In the compounds of the present invention, $R^1$ is preferably alkanoyloxy, such as unsubstituted alkanoyloxy (e.g., acetyloxy), or hydroxy; $R^2$ is preferably furyl or thienyl; and $R^3$ is preferably hydrogen, phenyl, substituted phenyl, phenylcarbonyl, substituted phenylcarbonyl, alkylcarbonyl, alkenylcarbonyl or alkoxycarbonyl such as t-butoxycarbonyl. $R^6$ is preferably hydrogen or a $C_{1-6}$ alkyl such as methyl.

Enzymes and Microorganisms

The enzyme or microorganism employed in the methods of the present invention may be any enzyme or microorganism having the ability to catalyze the stereoselective conversions as described herein. Various enzymes, such as esterases, lipases and proteases, regardless of origin or purity, are suitable for use in the present invention. The enzyme may, for example, be in the form of animal or plant enzymes or mixtures thereof, cells of microorganisms, crushed cells, extracts of cells, or of synthetic origin.

With respect to the use of microorganisms, the methods of the present invention may be carried out using any microbial cellular material having the ability to catalyze the stereoselective conversions as described herein. The cells may be used in the form of intact wet cells or dried cells such lyophilized, spray-dried or heat-dried cells. Cells may also be used in the form of treated cell material such as ruptured cells or cell extract.

The enzyme or microbial materials may be employed in the free state or immobilized on a support (for example, a polymeric resin) such as by physical adsorption or entrapment.

Exemplary genera of microorganisms suitable as sources of catalyzing enzymes include Mucor, Escherichia, Staphylococcus, Agrobacterium, Acinetobacter, Rhizopus, Aspergillus, Nocardia, Streptomyces, Trichoderma, Candida, Rhodotorula, Torulopsis, Proteus, Bacillus, Alcaligenes, Pseudomonas, Rhodococcus, Brevibacterium, Geotrichum, Enterobacter, Chromobacterium, Arthrobacter, Microbacterium, Mycobacterium, Saccharomyces, Penicillium, Methanobacterium, Botrytis, Chaetomium, Ophiobolus, Cladosporium and the like. The use of genetically engineered host cells is also contemplated.

Specific microorganisms suitable for use in the present processes include *Chromobacterium viscosum, Pseudomonas aeuriginosa* such as ATCC 25619, *Pseudomonas fluorescens, Pseudomonas putida* such as ATCC 31303, *Pseudomonas ovalis, Escherichia coli, Staphylococcus aureus, Alcaligenes faecalis, Streptomyces griseus, Pseudomonas cepacia, Candida rugosa* such as ATCC 14830, *Geotrichum candidum* such as ATCC 32345, *Streptomyces clavuligerus, Nocardia erthropolis, Nocardia asteraicdes, Mycobacterium phlei, Agrobacterium radiobacter, Aspergillus niger, Rhizopus oryzae* and the like. Two or more, as well as a single, species of microorganism may be employed when carrying out the instant processes.

The term "ATCC" as used herein refers to the accession number of the American Type Culture Collection, 12301 Parklawn Drive, Rockville, Md. 20852, the depository for the organism referred to.

The resolution methods of the instant invention may be carried out subsequent to the growth of the microorganism (s) employed, or concurrently therewith that is, in the latter case, by in situ fermentation and resolution. The growth of microorganisms may be achieved by one of ordinary skill in the art, for example, by the use of an appropriate medium containing nutrients such as carbon and nitrogen sources and trace elements.

Exemplary, commercially available enzymes suitable for use in the present invention include lipases such as Amano PS-30 (*Pseudomonas cepacia*), Amano GC-20 (*Geotrichum candidum*), Amano APF (*Aspergillus niger*), Amano AK (*Pseudomonas sp.*), Pseudomonas fluorescens lipase (Biocatalyst Ltd.), Amano Lipase P-30 (*Pseudomonas sp.*), Amano P (*Pseudomonas fluorescens*), Amano AY-30 (*Candida cylindracea*), Amano N (*Rhizopus niveus*), Amano R (*Penicillium sp.*), Amano FAP (*Rhizopus oryzae*), Amano AP-12 (*Aspergillus niger*), Amano MAP (*Mucor meihei*), Amano GC-4 (*Geotrichum candidum*), Sigma L-0382 and L-3126 (porcine pancrease), Lipase OF (Sepracor), Esterase 30,000 (Gist-Brocarde), KID Lipase (Gist-Brocarde), Lipase R (*Rhizopus sp.*, Amano), Sigma L-3001 (Wheat germ), Sigma L-1754 (*Candida cylindracea*), Sigma L-0763 (*Chromobacterium viscosum*) and Amano K-30 (*Aspergillus niger*). Additionally, exemplary enzymes derived from animal tissue include esterase from pig liver, α-chymotrypsin and pancreatin from pancreas such as Porcine Pancreatic Lipase (Sigma). Two or more, as well as a single, enzyme may be employed when carrying out the instant processes.

The preferred embodiments of the instant invention are described further in the following Reaction Schemes. While, for clarity, these Reaction Schemes illustrate the resolution of certain cis enantiomeric mixtures, it is understood that the embodiments as described apply to the resolution of the other enantiomeric mixtures of the present invention as well.

Reaction Scheme I:
Resolution by Esterification

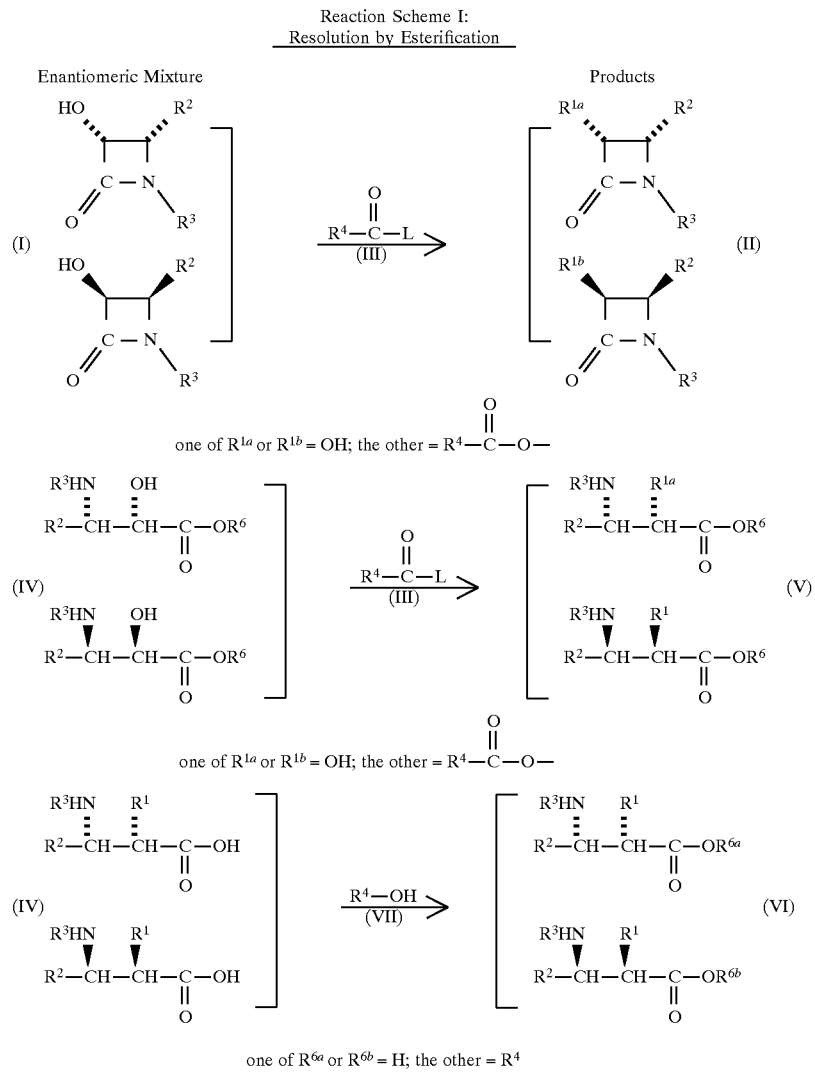

Reaction Scheme II
Resolution by Transesterification

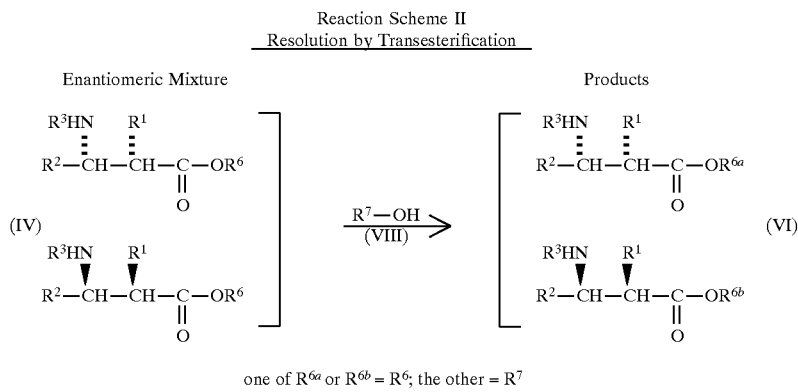

one of $R^{6a}$ or $R^{6b} = R^6$; the other = $R^7$

Mixtures I and IV may be stereoselectively esterified as illustrated in the above Reaction Scheme I, and mixture IV may be stereoselectively transesterified as illustrated in the above Reaction Scheme II.

(A) Acylation

Mixture I may be selectively esterified to form mixture II, and mixture IV may be selectively esterified to form mixture V by use of an acylating agent of the formula III:

$$R^4\text{—C(O)—L} \qquad (III).$$

In formula III, $R^4$ may be an alkyl, alkenyl, alkynyl, aryl, cycloalkyl, cycloalkenyl or heterocyclo group. Preferred $R^4$ groups in formula III are alkyl groups such as $C_{1-6}$ alkyl groups, especially methyl. L is a leaving group which may be displaced to form an ester group. Exemplary L groups include halogen atoms, hydroxyl, alkoxy, or alkenyloxy groups. Preferred L groups are alkenyloxy groups, most preferably $C_{1-6}$ alkenyloxy groups such as $CH_2$=CH—O— and $CH_2$=C($CH_3$)—O—. Any acylation agent of formula III which effects esterification may be employed, with isopropenyl acetate and vinyl acetate being particularly preferred.

(B) Esterification with Alcohol

Mixture IV may be selectively esterified to form mixture VI by use of an organic alcohol of the formula VII:

$$R^4\text{—OH} \qquad (VII).$$

In formula VII, $R^4$ may be an alkyl, alkenyl, alkynyl, aryl, cycloalkyl, cycloalkenyl or heterocyclo group. Alkyl groups, particularly $C_{1-6}$ alkyl groups, are preferred as $R^4$.

(C) Transesterification with Alcohol

Mixture IV may be selectively transesterified to form mixture VI by use of an alcohol of the formula VIII:

$$R^7\text{—OH} \qquad (VIII).$$

In formula VIII, $R^7$ may be an alkyl, alkenyl, alkynyl, aryl, cycloalkyl, cycloalkenyl or heterocyclo group, except that $R^7$ is not the same as $R^6$. It is preferred that the group $R^7$ be as distinct as possible from the group $R^6$ to facilitate subsequent separation of the compound bearing the group $R^7$—O—C(O)— from the compound bearing the group $R^6$—O—C(O)—. Thus, it is preferred to employ an alcohol of the formula VIII in which the $R^7$ group differs with respect to the group $R^6$ in terms of molecular weight, or otherwise imparts distinctive physical or chemical properties to the transesterified ester.

The esterification (acylation) procedure (A), and the esterification and transesterification procedures (B) and (C), are preferably carried out in an organic solvent. Exemplary solvents suitable for use in these processes include 1,1,2-trichloro-1,2,2-trifluoroethane, toluene, cyclohexane, benzene, hexane, heptane, isooctane, octane, methyl ethyl ketone, methyl isobutyl ketone and the like. Water is preferably added to the reaction mixture in small amounts. When present, the concentration of water in the reaction mixture is preferably from about 0.01% to about 1% based on the weight of solvent, or present in a concentration less than or equal to that where the organic solvent is saturated. Water is most preferably present in an amount of about 0.05% to about 0.5% based on the weight of solvent. The reaction solution preferably contains between about 5 to about 250 mg of the enantiomeric starting compounds per ml of solvent.

To carry out these processes, a compound III, VII or VIII is added to the reaction medium. Preferred molar ratios of the compound III: compounds of mixture I or IV are from about 1:1 to about 4:1; preferred molar ratios of the compound VII: compounds of mixture IV are from about 1:1 to about 4:1; and preferred molar ratios of the compound VIII: compounds of mixture IV are from about 1:1 to about 4:1.

The enzymes or microorganisms employed in these procedures are preferably lipases or esterases or microorganisms capable of producing these enzymes. Enzymes or microorganisms particularly preferred in these processes are Lipase PS-30 from *Pseudomonas sp.*, Lipase P-30 from *Pseudomonas sp.*, Lipase R from *Penicillium sp.*, Lipase OF, Lipase N from *Rhizopus niveus*, Lipase APF from *Aspergillus niger*, Lipase GC-20 from *Geotrichum candidum*, Lipase AK from *Pseudomonas sp.*, Lipase AY-30 from *Candida sp.*, and *Pseudomonas fluorescens* Lipase.

An enzyme may, for example, be used in its free state or in immobilized form. A preferred embodiment of the invention is that where an enzyme is adsorbed onto a suitable carrier, e.g., diatomaceous earth (porous Celite Hyflo Supercel), microporous polypropylene (Enka Accurel® polypropylene powder), or a nonionic polymeric adsorbent such as Amberlite® XAD-2 (polystyrene) or XAD-7 (polyacrylate) from Rohm and Haas Co. When employed to immobilize an enzyme, a carrier may control the enzyme particle size and prevent aggregation of the enzyme particles when used in an organic solvent. Immobilization can be accomplished, for example, by precipitating an aqueous solution of the enzyme with cold acetone in the presence of the Celite Hyflo Supercel followed by vacuum drying, or in the case of a nonionic polymeric adsorbent, incubating enzyme solutions with adsorbent on a shaker, removing excess solution and drying enzyme-adsorbent resins under vacuum. The enzyme is preferably added to the reaction solution to achieve concentrations ranging from about 5 to about 200 mg of enzyme per ml of solvent. While it is desirable to use the least amount of enzyme possible, the amount of enzyme required will vary depending upon the specific activity of the enzyme used.

These processes may also be carried out using microbial cells containing an enzyme having the ability to catalyze the stereoselective conversions. When using a microorganism to perform the resolution, these procedures are conveniently carried out by adding the cells and the enantiomeric mixture starting material to the desired reaction medium. Cells may be used in the form of intact cells, dried cells such as lyophilized, spray-dried or heat-dried cells, immobilized cells, or cells treated with organic solvents such as acetone or toluene. Cells may also be used in the form of treated cell material such as ruptured cells or cell extract. Cell extracts immobilized on Celite® or Accurel® polypropylene as described earlier may also be employed.

Incubation of the reaction medium is preferably at a temperature between about 4 and about 60° C. and is most preferably between about 30° to 50° C. The reaction time can be appropriately varied depending upon the amount of enzyme used and its specific activity. Reaction times may be reduced by increasing the reaction temperature and/or increasing the amount of enzyme added to the reaction solution.

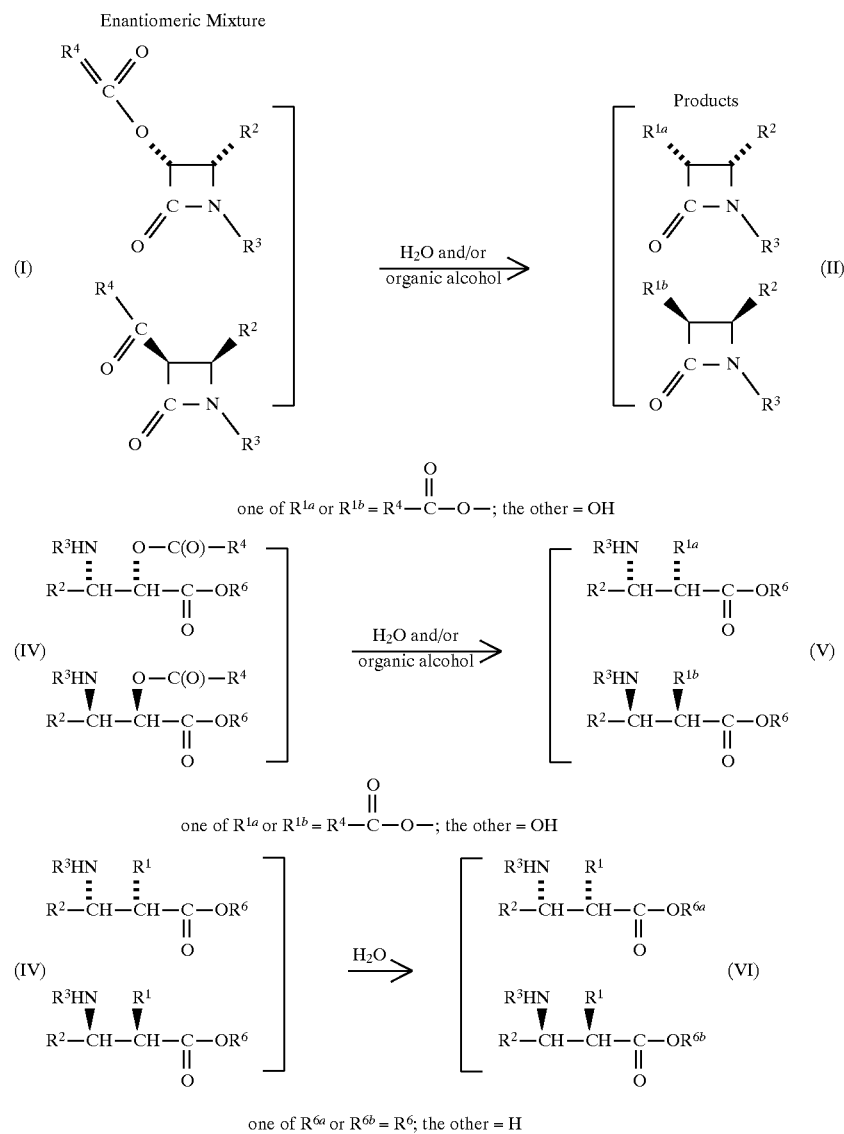

As can be seen from Reaction Scheme III above, mixtures I and IV may be stereoselectively hydrolyzed to form mixtures II and V, respectively, by use of water and/or an organic alcohol, and mixture IV may be stereoselectively hydrolyzed to form mixture VI by use of water. The groups $R^4$, forming part of $R^1$, and $R^6$ in the starting enantiomeric compounds are preferably alkyl, most preferably $C_{1-6}$ alkyl such as methyl.

A compound of the formula IX:

$$R^8\text{—OH} \tag{IX}$$

may be employed as the organic alcohol, where $R^8$ is an alkyl, alkenyl, alkynyl, aryl, cycloalkyl, cycloalkenyl or heterocyclo group, and is preferably alkyl such as methyl. Use of the organic alcohol IX may result in the formation of the by-product ester $R^4$—C(O)—$OR^8$. Use of water as the hydrolysis agent may result in the formation of the by-product acid $R^4$—C(O)—OH. To maintain a steady pH as these acidic by-products are generated, a base such as an alkali metal hydroxide may be added. When an organic alcohol IX is employed, an amount providing a molar ratio of compound IX: compounds of mixtures I or IV of from about 1:1 to about 4:1 is preferably added.

These processes preferably employ water-soluble enzymes capable of catalyzing stereoselective hydrolysis. Especially suitable for use with these processes are lipases and esterases, as well as pancreatin and α-chymotrypsin. Either the crude or purified forms of these enzymes, in free form or immobilized on a support (for example, on a resin such as XAD-7, XAD-2 or Accurel® resins), may be employed. Particularly preferred in these processes are Lipase PS-30 from *Pseudomonas sp.* (*Pseudomonas cepacia*) (Amano Int'l), Lipase P-30 (Amano) from *Pseudomonas sp.*, Lipase GC-20 *Geotrichum candidum* (Amano Int'l), Lipase N *Rhizopus niveus* (Amano Int'l), Lipase APF *Aspergillus niger* (Amano Int'l), Lipase AY-30 *Candida sp.* (Amano), Lipase AK *Pseudomonas sp.* (Amano Int'l), *Pseudomonas fluorescens* Lipase (Biocatalyst Ltd.), Esterase 30,000 (Gist-Brocarde), Lipase OF (Sepracor), KID Lipase (Gist-Brocarde), Lipase R (*Rhizopus sp.*, Amano Int.) and Porcine Pancreatic Lipase (Sigma Chem).

The above hydrolyses are preferably conducted in an aqueous, such as a buffered aqueous (e.g., phosphate buffer), medium or in an aqueous medium containing a miscible or immiscible organic solvent. For example, the reaction may be conducted in a biphasic solvent system comprising an organic phase, immiscible in water, and an aqueous phase. Use of a two phase solvent system may enhance the efficiency of such processes where the substrate material is insoluble in water.

Solvents for the organic phase of a biphasic solvent system may be any organic solvent immiscible in water, such as toluene, cyclohexane, xylene, trichlorotrifluoroethane and the like. The aqueous phase is conveniently of water, preferably deionized water, or a suitable aqueous buffer solution, especially a phosphate buffer solution. The biphasic solvent system preferably comprises between about 10 to 90 percent by volume of organic phase and between about 90 to 10 percent by volume of aqueous phase.

An amount of enantiomeric mixture starting material of from about 0.1 to about 100 mg per ml of reaction solution, and one or more enzymes in an amount of from about 0.1 to about 100 mg enzyme per mg of starting material to be hydrolyzed, is preferred.

The reaction mixture is preferably adjusted to and maintained at about pH 7.0, preferably with an aqueous alkali metal hydroxide, carbonate or bicarbonate.

The reaction time may be selected based on the enzyme, the temperature and the enzyme concentration. Temperatures of from about 4° C. to about 60° C. are preferably employed.

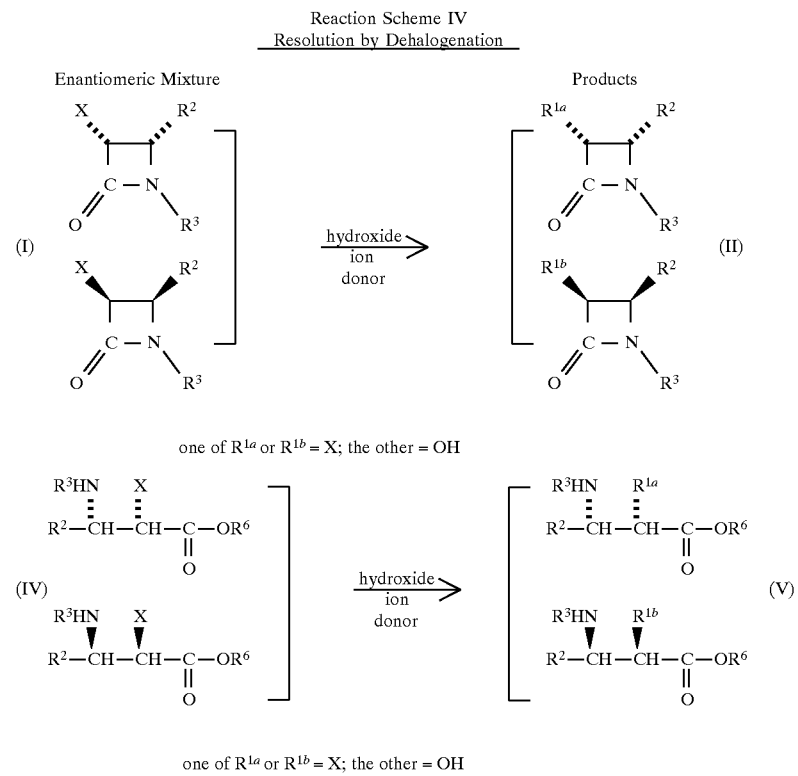

Reaction Scheme IV
Resolution by Dehalogenation

As can be seen from Reaction Scheme IV above, mixtures I and IV may be selectively dehalogenated to form mixtures II and V, respectively, wherein X denotes a halogen atom.

Any compound capable of effecting these reactions may be employed as the hydroxide ion donor. Exemplary such compounds are selected from water, alkali or alkaline earth metal hydroxides such as sodium and potassium hydroxide, and ammonium hydroxides such as quaternary ammonium hydroxides, for example, those of the formula $(R^9)_4NOH$ where $R^9$ is hydrogen or alkyl, particularly potassium hydroxide and water. Amounts of the hydroxide ion donor added are preferably those providing a molar ratio of hydroxide ion donor: mixture I or IV enantiomeric starting material of from about 1:1 to about 4:1.

A reaction medium containing water and an organic solvent such as toluene or hexane is preferably employed. The enantiomeric starting materials are preferably employed in an amount of from about 1 mg to about 100 mg per ml of solvent.

Enzymes or microorganisms employed in the dehalogenation reaction are preferably selected from the genera Pseudomonas, Trichoderma, Acinetobacter, Alcaligenes, Nocardia, Mycobacterium, Rhodococcus, Methanobacterium, Proteus, or enzymes derived therefrom, and are preferably employed in amounts of from about 0.1 mg to about 10 mg enzyme per mg of starting material to be dehalogenated.

Temperatures of from about 4° C. to about 50° C. are preferably employed.

Separation

The products of the stereoselective conversions may be isolated and purified by methodologies such as extraction, distillation, crystallization, column chromatography, and the like.

A preferred method for separating the product mixtures formed by the methods of the present invention is by liquid-liquid extraction.

Utility

Taxanes are diterpene compounds containing the taxane carbon skeleton:

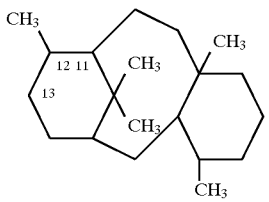

which skeleton may contain ethylenic unsaturation in the ring system thereof. Of particular interest are taxanes having the above carbon skeleton wherein the 11,12-positions are bonded through an ethylenic linkage, and the 13-position contains a side chain. Pharmacologically active taxanes, such as taxol analogues, may be used as antitumor agents to treat patients suffering from cancers such as ovarian cancer, melanoma, breast, colon or lung cancer, and leukemia.

The resolved compounds obtained by the methods of the present invention are particularly useful as intermediates in forming the aforementioned C-13 side chain on the taxane skeleton. The addition of such a side chain, in and of itself, may impart an increased or more desirable pharmacological activity to the taxane product, or may form a taxane product which is more readily converted to a taxane having an increased or more desirable pharmacological activity than the starting compound.

The compounds resolved according to the methods of the present invention may be modified prior to use in side chain formation. For example, resolved compounds containing an azide group $N_3$ as the group W may be treated by a reducing agent to form an amine group which may be substituted.

Exemplary methods for side chain formation, and taxane products which may be formed employing such methods, include those described in European Patent Application No. 534,708; U.S. patent application Ser. No. 08/080,704, filed Jun. 28, 1993; U.S. patent application Ser. No. 08/029,819, filed Mar. 11, 1993; U.S. patent application Ser. No. 07/996,455, filed Dec. 24, 1992; U.S. patent application Ser. No. 08/062,687, filed May 20, 1993; U.S. patent application Ser. No. 07/981,151, filed Nov. 24, 1992; and U.S. patent application Ser. No. 07/995,443, filed Dec. 23, 1992; all of which aforementioned documents are incorporated herein by reference.

Salts or solvates of reactants or products may be employed or prepared as appropriate or desired in the methods of the present invention.

The methods of the present invention are further described by the following examples. These examples are illustrative only, and are in no way intended to limit the scope of the instant claims.

EXAMPLE 1

Synthesis of Substrate for Resolution (±)-cis-3-Acetoxy-4-(2'-furanyl)azetidin-2-one (A) Preparation of N,N'-[(2'-Furanyl)methyl]-2-furanmethanimine

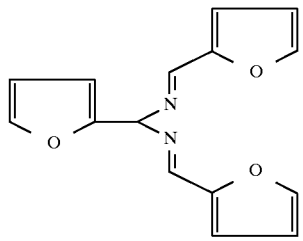

To a 3 L 2-necked round bottom flask equipped with a thermometer and mechanical stirrer was added 2-furaldehyde (furfural, 311 ml, 3.75 mol, Aldrich) and 2-propanol (IPA, 0.75 L, reagent grade). With stirring, 1.5 L of concentrated $NH_4OH$ (aq., ~30%) (22.2 mol) was added in one portion. An exotherm (~35° C.) was noted in the first two hours. The resulting beige powder was isolated by filtration (Whatman No. 1), washed with water (1.5 L) and dried overnight in vacuo at 30° C. This gave 255.3 g (76.1% yield) of the title hydrofuramide as a beige powder (melting point (mp)=116°–117° C.). The $R_f$ of the title hydrofuramide was 0.5 (ethyl acetate (EtOAc)/Hexane, 1:1; UV visualization).

(B) Preparation of (±)-cis-3-Acetoxy-4-( 2'-furanyl)azetidin-2-one (i) Staudinger Reaction

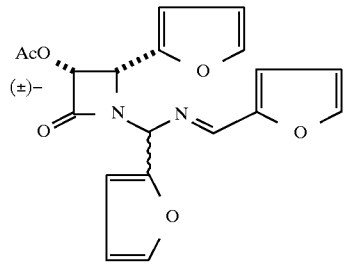

"Ac" denotes acetyl ($CH_3$—C(O)—)

"(±)" denotes, with respect to the 3-and 4-position substituents on the azetidine ring, a racemate of the cis enantiomers.

To a 2 L 3-necked round bottom flask equipped with a thermometer, pressure equalizing dropping funnel and mechanical stirrer was added the hydrofuramide title product of step (A) above (80.48 g, 0.300 mol) and ethyl acetate (1.0 L, reagent grade). This mixture was cooled under argon to 4° C. at which point triethylamine (50.2 ml, 0.360 mol, Aldrich) was added in one portion. The dropping funnel was charged with acetoxyacetyl chloride (37.0 ml, 0.341 mol, Aldrich) and ethyl acetate (0.50 L, reagent grade) and this solution was added dropwise over a period of 1 hour. After an additional 2 hours, the stirring was discontinued and the reaction vessel sealed (Parafilm "M"®) and moved to the cold room (4° C.) for a further 15 hours. The heterogeneous reaction mixture was allowed to warm to 22° C. (~1 hour) with stirring and transferred to a 4.0 L separatory funnel and washed with aqueous $NH_4Cl$ (sat) (500 ml). Both layers were filtered through glass microfibre filter paper (Whatman) to remove a fine, black suspension. Removal of the particulate material aided in phase separation. The filter cake was rinsed with ethyl acetate (50 ml) and the filtrate transferred back to the separatory funnel and the aqueous layer (pH=6.3) removed. The organic layer was then washed with another portion of aqueous $NH_4Cl$ (sat) (250 ml; pH=5.9), aqueous $NaHCO_3$ (sat) (400 ml; pH=8.6) and aqueous NaCl (sat) (400 ml; pH=7.0),. The organic layer was filtered through glass microfibre filter paper (Whatman) and divided into 2 equal portions (750 ml each). These solutions were used directly in the next step.

(ii) Deprotection

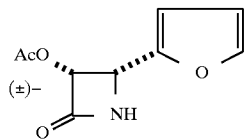

To two 2.0 L Parr flasks each containing 10% palladium on activated carbon (2×6.00 g, Aldrich) was added, under a stream of argon, the organic layers from above (2×750 ml; Step (B)(i)). This mixture was treated with hydrogen (4 atm) for 1 day at ambient temperature. The catalyst was removed by filtration through a pad of Celite® and the filter cake rinsed with ethyl acetate (100 ml). The filtrate was transferred to a 4.0 L separatory funnel and washed twice with 1N HCl (500 ml, 250 ml; pH=0.76). The aqueous washings were combined and re-extracted with ethyl acetate (500 ml) and the organic layers were combined and washed with aqueous $NaHCO_3$ (sat) (400 ml; pH=8.34) and aqueous NaCl (sat) (400 ml; pH=7.5). The organic layer was dried over $MgSO_4$ (~100 g) and treated with activated decolorizing charcoal (30 g, BDH). After 15 minutes, the mixture was filtered through a pad of Celite® and concentrated in vacuo to 160 ml, cooled overnight (4° C.) and the precipitated solid isolated by filtration through filter paper (Whatman No. 1). The filter cake was rinsed with diethyl ether and hexane (100 ml of each) to provide, after drying in vacuo, 35.98 g (61.4% yield from the above hydrofuramide) of the title product (±)-cis-3-acetoxy-4-(2'-furanyl)azetidin-2-one as white needles (mp 118°–119° C.). HPLC quantitative analysis demonstrated 8.10 g of the title product in the mother liquor. The activity yield, from the above hydrofuramide, was therefore 75.3%.

EXAMPLE 2

Stereoselective Hydrolysis of (±)-cis-3-Acetoxy-4-(2'-furanyl)azetidin-2-one

The substrate employed in this Example was the racemate:

I

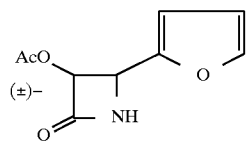

prepared as the title product of Example 1. The products of the stereoselective hydrolysis of this Example were the compounds:

(+)-cis-3-Acetoxy-4-(2'-furanyl)azetidin-2-one:

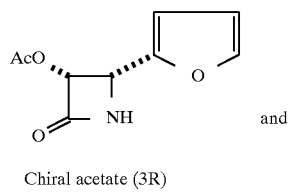

Chiral acetate (3R)

(−)-cis-3-Hydroxy-4-(2'-furanyl)azetidin-2-one:

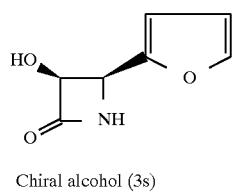

Chiral alcohol (3s)

The stereoselective hydrolysis was conducted as follows. A reaction mixture in 1 L of 25 mM potassium phosphate buffer pH 7.0 was prepared containing 10 grams of substrate and 100 grams of lipase PS-30 from *Pseudomonas sp.* (Amano International Co.). The reaction was carried out at 30° C., 150 revolutions-per-minute (RPM) agitation. During the reaction, the pH of the reaction mixture was maintained at 7.0 with 5N NaOH using a pH stat. The hydrolysis reaction was monitored by high pressure liquid chromatography (HPLC). Periodically, samples (1 ml) were taken and extracted with 10 ml of ethyl acetate. The ethyl acetate layer was separated and evaporated to dryness and analyzed by HPLC (as described following) for the substrate and product concentrations and the optical purity of the product. The results obtained are as shown in the following Table 1.

TABLE 1

| Reaction Time (Hours) | Conversion (% Product IIb) | Yield (% Product IIa) | Optical Purity of Product IIa (%) |
|---|---|---|---|
| 4 | 18 | 82 | — |
| 8 | 34 | 66 | — |
| 12 | 46 | 54 | — |
| 16 | 51 | 49 | >99.4 |

In Process Chiral HPLC Assays

Periodically, during the reaction as described above, a 1 ml sample was taken and extracted with 10 ml of ethyl acetate contained in a 50 ml screw-cap tube. The ethyl acetate layer (5 ml) was removed, evaporated under a gentle stream of nitrogen. The residue was dissolved in 2 ml of mobile phase (hexane:absolute ethanol, 95:5). The mobile phase was passed through 0.2 μm Lydex filter and about 1 ml of the filtrate was transferred to a crimp vial for HPLC analysis. HPLC conditions:
Hewlett Packard 1090 chromatogram.
Column: Chiralcal AD
Mobile Phase: hexane:absolute ethanol, 95:5
Column Temperature: Ambient
Flow Rate: 1 ml/min
Detection: 210 nm.

The retention times for the two enantiomers of racemic acetate were 23.2 min and 28.9 min, respectively. The retention times for the two enantiomers of racemic alcohol were 63.9 min and 74.8 min, respectively.

EXAMPLE 3

Stereoselective Hydrolysis of (±)-cis-3-Acetoxy-4-(2'-furanyl)azetidin-2-one using Immobilized Lipase PS-30 Enzyme The substrate employed, and the products obtained, were those of Example 2 above.

Immobilization of Enzyme

Three different carriers—XAD-7 (Amberlite XAD-7 non-ionic polymeric adsorbent, 20–60 mesh polyacrylate resin), XAD-2 (Amberlite XAD-nonionic polymeric adsorbent, 20–60 mesh polystyrene resin) and Accurel PP (polypropylene resin 200–400 microns)—were used for the immobilization procedures.

Crude Amano PS-30 lipase (10 g) was dissolved in 25 ml of distilled water and centrifuged at 10,000 RPM for 10 minutes to obtain clear supernatant. The carrier (1.3 g) in a 25 ml vial was washed 5 times with methanol and added to enzyme solution in a flask and gently agitated on a gyrotory shaker at room temperature. Adsorption of enzyme to the carrier was checked periodically by lipase assay (Sigma olive oil emulsion as substrate) and by protein remaining in filtrate. About 68%, 71% and 98% adsorption efficiencies were obtained using XAD-7, XAD-2 and Accurel resins, respectively. After complete immobilization (20 to 24 hours), the carrier-enzyme slurry was filtered through a millipore filter and the carrier was washed with about 300 ml of distilled water. Subsequently, the carrier containing the immobilized lipase was dried in a vacuum oven at room temperature.

Use of Immobilized Enzyme

Immobilized enzyme was employed for the enzymatic hydrolysis reaction described in Example 2. Reaction mixtures were prepared which contained 30 ml of 25 mM potassium phosphate buffer pH 7.0 containing 300 mg of substrate as described in Example 2, and 300 mg of the above prepared immobilized Lipase PS-30. The reactions were conducted as described in Example 2. The results obtained are shown in the following Table 2.

TABLE 2

| Immobilized Support | Reaction Time (Hours) | Conversion (% Product IIb) | Yield (% Product IIa) | Optical Purity of Product IIa (%) |
| --- | --- | --- | --- | --- |
| XAD-2 | 3 | 53 | 47 | 99.0 |
| XAD-7 | 3 | 54 | 46 | 99.3 |
| Accurel PP | 3 | 51 | 49 | 99.5 |

EXAMPLE 4

Stereoselective Hydrolysis of (±)-cis-3-Acetoxy-4-(2'-furanyl)azetidin-2-one

The substrate employed, and products obtained, were those of Example 2 above. In this Example, a number of reactions were run in which lipases from different sources were employed.

In each reaction, the reaction mixture, in 20 ml of 25 mM phosphate buffer, pH 7.0 contained 1 gram of crude lipase and 200 mg of substrate. The reactions were conducted at 25° C. in a pH stat at pH 7.0. The results obtained are shown in the following Table 3.

TABLE 3

| Enzyme | Source | Reaction Time (Hours) |
| --- | --- | --- |
| Lipase PS-30 Pseudomonas sp. | Amano Int. | 16 |
| Lipase AY-30 Candida sp. | Amano Int. | 8 |
| Lipase AK Pseudomonas sp. | Amano Int. | 16 |
| Pseudomonas fluorescens | Biocatalyst Ltd. | 16 |
| Porcine pancreatic Lipase | Sigma | 19 |
| Esterase 30,000 | Gist-Brocarde | 24 |
| Lipase OF | Sepracor | 8 |
| KID Lipase | Gist-Brocarde | 48 |
| Lipase R. Rhizopus sp. | Amano Int. | 24 |

| Conversion (% Product IIb) | Yield (% Product IIa) | Optical Purity of Product IIa (%) |
| --- | --- | --- |
| 52 | 48 | >99.5 |
| 55 | 45 | 99.0 |
| 53 | 47 | 99.3 |
| 55 | 45 | 98.8 |
| 52 | 48 | 99.8 |
| 51 | 49 | 95 |
| 56 | 44 | 99.5 |
| 52 | 48 | 95 |
| 56 | 44 | 99.0 |

EXAMPLE 5

Stereoselective Acetylation (Esterification) of (±)-cis-3-Hydroxy-4-(2'-furanyl)azetidin-2-one The substrate employed in this Example was the racemate:

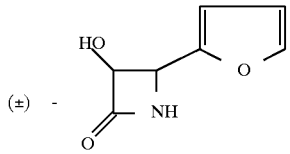

prepared by chemical hydrolysis (using $Na_2CO_3$) of the corresponding racemic acetate. The products of the stereoselective acetylation of this Example were the compounds:

(+)-cis-3-hydroxy-4-(2'-furanyl)azetidin-2-one:

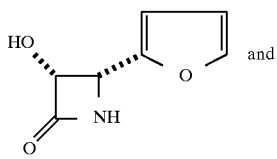

and

IIa (−)-cis-3-acetoxy-4-(2′-furanyl)azetidin-2-one:

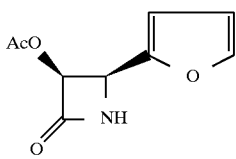
IIb

In this Example, a number of reactions were run in which lipases from different sources were employed to achieve stereoselective acetylation. In each reaction, the reaction mixture, in 25 ml of toluene, contained 1 gram of crude lipase and 100 mg of substrate, 800 mg of isopropenyl acetate, and 0.05% water. The reactions were conducted at 30° C. and 100 RPM on a shaker. The products and substrate were analyzed by HPLC. The results which were obtained are shown in the following Table 4.

TABLE 4

| Enzyme | Source | Conversion (% Product IIb) | Yield (% Product IIa) | Optical Purity of Product IIa (%) |
| --- | --- | --- | --- | --- |
| Lipase PS-30 | Amano Int. | 52 | 48 | 99.5 |
| Lipase AY-30 | Amano Int. | 55 | 45 | 99.0 |
| Lipase R | Amano Int. | 51 | 49 | 96.8 |
| Pseudomonas fluorescens | Biocatalyst Inc. | 54 | 46 | 98.8 |
| Lipase OF | Sepracor | 52 | 48 | 99.0 |
| Porcine Pancreatic Lipase | Sigma | 54 | 46 | 98.0 |

EXAMPLE 6

Stereoselective Hydrolysis: Evaluation of Various Enzymes

The substrate employed, and products obtained, were those of Example 2 above. For each stereoselective hydrolysis reaction, a reaction mixture in 20 ml of 25 mM potassium phosphate buffer pH 7.0 was prepared containing 200 mg of substrate and 1 gram of enzyme (see Table 5 for enzyme). The reaction was carried out at 30° C., 150 revolutions-per-minute (RPM) agitation. During the reaction, the pH of the reaction mixture was maintained at 7.0 with 1N NaOH using a pH stat. The hydrolysis reaction was monitored by high pressure liquid chromatography. Periodically, samples (1 ml) were taken and extracted with 4 ml of ethyl acetate. The ethyl acetate layer was separated and evaporated to dryness and analyzed by HPLC for the substrate and product concentrations and the optical purity of the product. The results obtained are shown in the following Table 5.

TABLE 5

| Enzyme | Source | Reaction Time (Hours) | Yield (% Product IIa) | Optical Purity of Product IIa (%) |
| --- | --- | --- | --- | --- |
| Lipase PS-30 | Amano Int. | 16 | 48 | >99.5 |
| Lipase AY-30 | Amano Int. | 8 | 46 | >99 |
| Lipase AK | Amano Int. | 16 | 47 | >99 |
| Pseudomonas fluorescens Lipase | Biocatalysts Ltd. | 16 | 45 | >99 |
| Porcina Pancreatic Lipase | Sigma | 19 | 47 | 98.8 |

TABLE 5-continued

| Enzyme | Source | Reaction Time (Hours) | Yield (% Product IIa) | Optical Purity of Product IIa (%) |
| --- | --- | --- | --- | --- |
| Esterase 30,000 | Gist/Brocarde | 24 | 35 | 99 |
| Lipase OF | Sepracor | 8 | 44 | 99 |
| KID Lipase | Gist/Brocarde | 48 | 38 | 95 |
| Lipase R | Amano Int. | 24 | 44 | 99 |

EXAMPLE 7

Kinetics of Resolution of (±)-cis-3-Acetoxy-4-(2′-furanyl)azetidin-2-one by Immobilized Lipase PS-30

The substrate employed, and products obtained, were the same as those of Example 2 above.

A reaction mixture in 8.5 L of 25 mM potassium phosphate buffer pH 7.0 was prepared containing 85 grams of substrate, and 85 grams of Lipase PS-30 from Pseudomonas sp. (Amano International Co.). Lipase PS-30 was immobilized on Accural polypropylene and used in the reaction mixture. The reaction was carried out at 30° C., 150 revolutions-per-minute (RPM) agitation. During the reaction, the pH of the reaction mixture was maintained at 7.0 with 5N NaOH using a pH stat. The hydrolysis reaction was monitored by high pressure liquid chromatography. Periodically, samples (1 ml) were taken and extracted with 4 ml of ethyl acetate. The ethyl acetate layer was separated and evaporated to dryness and analyzed by HPLC for the substrate and product concentrations and the optical purity of the product. The results which were obtained are shown in the following Table 6.

TABLE 6

| Reaction Time (Hours) | A-Acetate (mg/ml) | B-Acetate (mg/ml) | A-Alcohol (mg/ml) |
| --- | --- | --- | --- |
| 0 | 6.2 | 5.2 | 0 |
| 1 | 2.1 | 5.2 | 2.9 |
| 2 | 0.65 | 5.2 | 4.1 |
| 3 | 0.19 | 5.1 | 4.3 |
| 4 | 0.1 | 5 | 4.9 |
| 5 | trace | 4.95 | 4.9 |
| 6 | trace | 4.9 | 4.9 |

| Reaction Time (Hours) | B-Alcohol (mg/ml) | Optical Purity B-Acetate (%) | Optical Purity A-Alcohol (%) |
| --- | --- | --- | --- |
| 0 | 0 | 50 | >99 |
| 1 | 0 | 72 | >99 |
| 2 | 0 | 89.6 | >99 |
| 3 | trace | 98.5 | >99 |
| 4 | trace | 98.5 | >99 |
| 5 | 0.13 | >99 | 97 |
| 6 | 0.15 | >99 | 97 |

"A-Acetate" had the following structure:

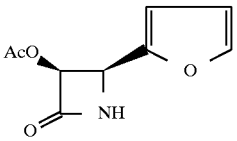

TABLE 6-continued

"B-Acetate" had the following structure:

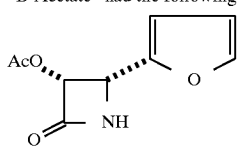

"A-Alcohol" had the following structure:

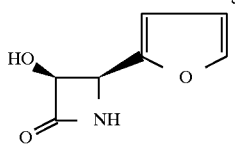

"B-Alcohol" had the following structure:

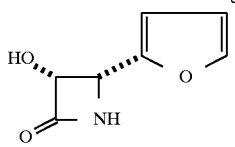

EXAMPLE 8

Stereoselective Esterification of (±)-cis-3-Hydroxy-4-(2'-furanyl)azetidin-2-one In this Example, the substrate employed, and products obtained, were the same as those of Example 5. A reaction mixture in 10 ml of methyl ethyl ketone (MEK) was prepared containing 20 grams of substrate, 1 gram of enzyme (see Table 7) and 0.4 ml isopropenyl acetate as acyl donor. The reaction was carried out at 30° C., 150 revolutions-per-minute (RPM) agitation. The esterification reaction was monitored by high pressure liquid chromatography (described following) to determine substrate and product concentrations and the optical purity of the product. The results obtained are as shown in the following Table 7.

TABLE 7

| Enzyme | Source | Reaction Time (Hours) | Yield of Chiral acetate (%) |
|---|---|---|---|
| Lipase PS-30 | Amano Int. | 96 | 50.5 |
| Lipase AY-30 | Amano Int. | 120 | 51 |
| Lipase AK | Amano Int. | 120 | 49 |
| Lipase OF | Sepracor | 96 | 49.5 |

| Enzyme | Source | Optical Purity of acetate (%) | Yield of Chiral alcohol (%) | Optical Purity of alcohol (%) |
|---|---|---|---|---|
| Lipase PS-30 | Amano Int. | 99.5 | 49.5 | 99 |
| Lipase AY-30 | Amano Int. | 99 | 49 | 99 |
| Lipase AK | Amano Int. | 99.5 | 51 | 99 |
| Lipase OF | Sepracor | 99.4 | 50.5 | 99 |

HPLC Method

The substrate and products were analyzed in the above Example by HPLC. A Nova Pak C18 reverse phase column (3.9×150 mm) column was used. The mobile phase was 15% acetonitrile in water and the flow rate was 1 ml/min. The detection wavelength was 227 nm. The retention times for alcohol and acetate were 2.7 min and 14.9 min, respectively.

The optical purity of chiral acetate was determined by chiral HPLC. A Chiralpak AS column was used. The mobile phase consisted of hexane:ethanol (96:4) which was used at 1 ml/min at ambient temperature. The detection wavelength was 210 nm. The retention times for the two enantiomers of racemic acetate were 23.7 min and 20.9 min, respectively. The retention times for the two enantiomers of racemic alcohol were 63.9 min and 74.8 min, respectively.

What is claimed is:

1. A method for the resolution of a mixture I comprising the enantiomers Ia and Ib, where $R^1$ is in the cis position relative to $R^2$ in both Ia and Ib, or where $R^1$ is in the trans position relative to $R^2$ in both Ia and Ib:

and

to form a mixture II comprising the compounds IIa and IIb, where $R^{1a}$ and $R^{1b}$ are in the cis position relative to $R^2$ in both IIa and IIb, or where $R^{1a}$ and $R^{1b}$ are in the trans position relative to $R^2$ in both IIa and IIb, in each case corresponding to the position of $R^1$ in mixture I:

and

where $R^1$ is —O—C(O)—$R^4$, and $R^4$ is alkyl or alkenyl;

one of $R^{1a}$ or $R^{1b}$ is the same as $R^1$ and the other of $R^{1a}$ or $R^{1b}$ is hydroxyl;

$R^2$ is furyl or thienyl; and $R^3$ is hydrogen or aryl;

comprising the step of contacting said mixture I, in the presence of water and/or an organic alcohol, with an enzyme which is selected from the group consisting of lipases derived from Pseudomonas, Candida, and Rhizopus, and porcine pancreatic lipase, and which is capable of catalyzing the stereoselective hydrolysis of said mixture I to provide said mixture II, and effecting said conversion.

2. The method of claim 1, wherein a mixture I comprising the enantiomers Ia(1) and Ib(1) is resolved:

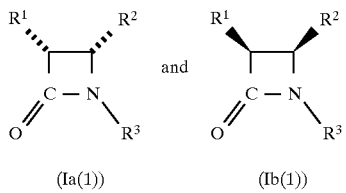

(Ia(1))       (Ib(1))

to form a mixture II comprising the compounds IIa(1) and IIb(1):

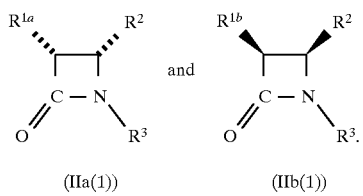

(IIa(1))       (IIb(1))

3. The method of claim 2, wherein, in said mixture I comprising Ia(1) and Ib(1):

$R^1$ is alkanoyloxy;

$R^2$ is furyl or thienyl; and $R^3$ is hydrogen, phenyl or substituted phenyl.

4. The method of claim 3, wherein said mixture I comprises (±)-cis-3-acetoxy-4-(2'-furanyl)azetidin-2-one and said mixture II comprises (+)-cis-3-acetoxy-4-(2'-furanyl)azetidin-2-one and (−)-cis-3-hydroxy-4-(2'-furanyl)azetidin-2-one.

5. The method of claim 1, wherein said enzyme is immobilized on a support.

6. The method of claim 1, wherein, further, the non-enantiomeric compounds IIa and IIb of said mixture II obtained are separated by a separation step.

7. The method of claim 6, wherein said separation step is an extraction, distillation, crystallization, or column chromatography step.

8. The method of claim 1, comprising the further step of preparing a taxane bearing a C-13 sidechain, wherein said sidechain is formed using at least one of the non-enantiomeric compounds IIa or IIb of said mixture II.

9. A method for the resolution of a mixture I comprising the enantiomers Ia and Ib, where $R^1$ is in the cis position relative to $R^2$ in both Ia and Ib, or where $R^1$ is in the trans position relative to $R^2$ in both Ia and Ib:

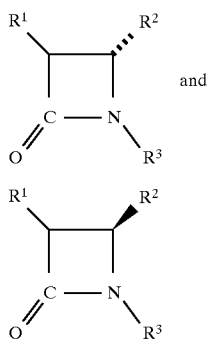

to form a mixture II comprising the compounds IIa and IIb, where $R^{1a}$ and $R^{1b}$ are in the cis position relative to $R^2$ in both IIa and IIb, or where $R^{1a}$ and $R^{1b}$ are in the trans position relative to $R^2$ in both IIa and IIb, in each case corresponding to the position of $R^1$ in mixture I:

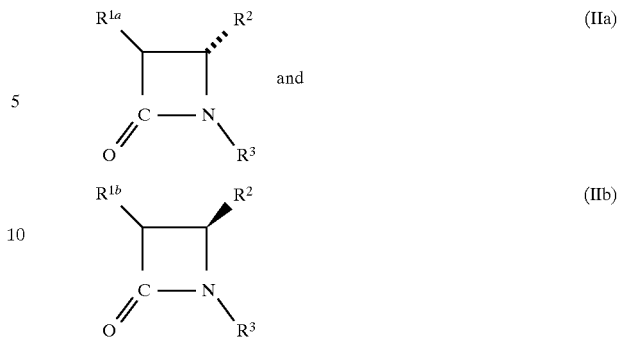

where $R^1$ is hydroxyl;

one of $R^{1a}$ or $R^{1b}$ is hydroxyl and the other of $R^{1a}$ or $R^{1b}$ is $R^4$—C(O)—O—, and $R^4$ is alkyl or alkenyl;

$R^2$ is furyl or thienyl; and $R^3$ is hydrogen or aryl;

comprising the step of contacting said mixture I, in the presence of a compound III:

where $R^4$ is as defined above for $R^{1a}$ or $R^{1b}$ and L is a leaving group, with an enzyme which is selected from the group consisting of lipases derived from Pseudomonas, Candida, and Rhizopus, and porcine pancreatic lipase, and which is capable of catalyzing the stereoselective esterification of said mixture I to provide said mixture II, and effecting said conversion.

10. The method of claim 9, wherein a mixture I comprising the enantiomers Ia(1) and Ib(1) is resolved:

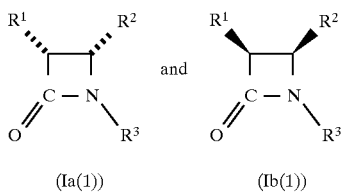

(Ia(1))       (Ib(1))

to form a mixture II comprising the compounds IIa(1) and IIb(1):

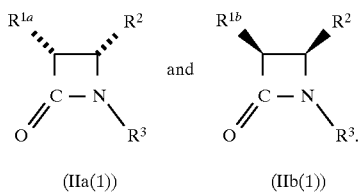

(IIa(1))       (IIb(1))

11. The method of claim 10, wherein, in said mixture II comprising IIa(1) and IIb(1):

$R^{1a}$ or $R^{1b}$ is alkanoyloxy;

$R^2$ is furyl or thienyl; and $R^3$ is hydrogen, phenyl or substituted phenyl.

12. The method of claim 11, wherein said mixture I comprises (±)-cis-3-hydroxy-4-(2'-furanyl)azetidin-2-one, said mixture II comprises (+)-cis-hydroxy-4-(2'-furanyl)azetidin-2-one and (−)-cis-3-acetoxy-4-(2'-furanyl)azetidin-2-one, and said compound of the formula III is isopropenyl acetate.

13. The method of claim 9, wherein said enzyme is immobilized on a support.

14. The method of claim 9, wherein, further, the non-enantiomeric compounds IIa and IIb of said mixture II obtained are separated by a separation step.

15. The method of claim 14, wherein said separation step is an extraction, distillation, crystallization, or column chromatography step.

16. The method of claim 9, comprising the further step of preparing a taxane bearing a C-13 sidechain, wherein said sidechain is formed using at least one of the non-enantiomeric compounds IIa or IIb of said mixture II.

17. A method for the resolution of a mixture I comprising the enantiomers Ia and Ib, where $R^1$ is in the cis position relative to $R^2$ in both Ia and Ib, or where $R^1$ is in the trans position relative to $R^2$ in both Ia and Ib:

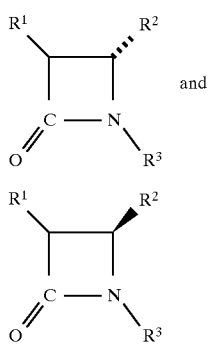

to form a mixture II comprising the compounds IIa and IIb, where $R^{1a}$ and $R^{1b}$ are in the cis position relative to $R^2$ in both IIa and IIb, or where $R^{1a}$ and $R^{1b}$ are in the trans position relative to $R^4$ in both IIa and IIb, in each case corresponding to the position of $R^1$ in mixture I:

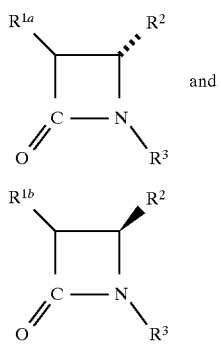

where $R^1$ is —O—C(O)—$R^4$, and $R^4$ is alkyl or alkenyl;

one of $R^{1a}$ or $R^{1b}$ is the same as $R^1$ and the other of $R^{1a}$ or $R^{1b}$ is hydroxyl;

$R^2$ is furyl or thienyl; and $R^3$ is hydrogen or aryl;

comprising the step of contacting said mixture I, in the presence of water and/or an organic alcohol, with an enzyme which is selected from the group consisting of KID lipase, lipase OF and Esterase 30,000, and which is capable of catalyzing the stereoselective hydrolysis of said mixture I to provide said mixture II, and effecting said conversion.

18. The method of claim 17, wherein a mixture I comprising the enantioners Ia(1) and Ib(1) is resolved:

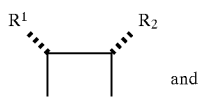

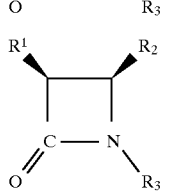

to form a mixture II comprising the compounds IIa(1) and IIb(1):

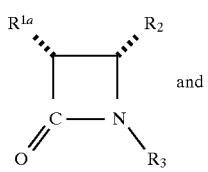

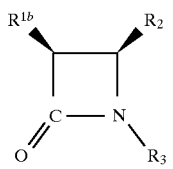

19. The method of claim 18, wherein, in said mixture I comprising Ia(1) and Ib(1):

$R^1$ is alkanoyloxy;

$R^2$ is furyl or thienyl; and $R^3$ is hydrogen, phenyl or substituted phenyl.

20. The method of claim 19, wherein said mixture I comprises (±)-cis-3-acetoxy-4-(2'-furanyl)azetidin-2-one and said mixture II comprises (+)-cis-3-acetoxy-4-(2'-furanyl)azetidin-2-one and (−)-cis-3-hydroxy-4-(2'-furanyl)azetidin-2-one.

21. The method of claim 17, wherei said enzyme is immobilized on a support.

22. The method of claim 17, wherein, further, the non-enantiomeric compounds IIa and IIb of said mixture II obtained are separated by a separation step.

23. The method of claim 22, wherein said separation step is an extraction, distillation, crystallization, or column chromatography step.

24. The method of claim 17, comprising the further step of preparing a taxane bearing a C-13 sidechain, wherein said sidechain is formed using at least one of the non-enantiomeric compounds IIa or IIb of said mixture II.

25. A method for the resolution of a mixture I comprising the enantiomers Ia and Ib, where $R^1$ is in the cis position relative to $R^2$ in both Ia and Ib, or where $R^1$ is in the trans position relative to $R^2$ in both Ia and Ib:

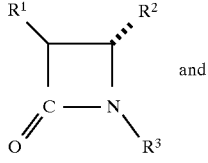

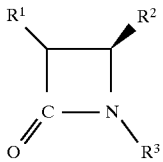

(Ib)

to form a mixture II comprising the compounds IIa and IIb, where $R^{1a}$ and $R^{1b}$ are in the cis position relative to $R^2$ in both IIa and IIb, or where $R^{1a}$ and $R^{1b}$ are in the trans position relative to $R^2$ in both IIa and IIb, in each case corresponding to the position of $R^1$ in mixture I:

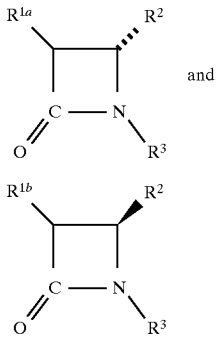

(IIa)

and (IIb)

where $R^1$ is hydroxyl;

one of $R^{1a}$ or $R^{1b}$ is hydroxyl and the other of $R^{1a}$ or $R^{1b}$ is $R^4$—C(O)—O—, and $R^4$ is alkyl or alkenyl;

$R^2$ is furyl or thienyl; and $R^3$ is hydrogen or aryl;

comprising the step of contacting said mixture I, in the presence of a compound III:

(III)

where $R^4$ is as defined above for $R^{1a}$ or $R^{1b}$ and L is a leaving group, with an enzyme which is selected from the group consisting of KID lipase, lipase OF and Esterase 30,000, and which is capable of catalyzing the stereoselective esterification of said mixture I to provide said mixture II, and effecting said conversion.

26. The method of claim 25, wherein a mixture I comprising the enantiomers Ia(1) and Ib(1) is resolved:

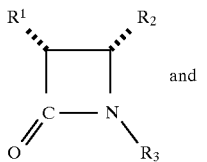

(Ia(1))

and

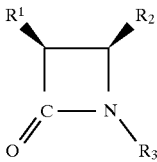

(Ib(1))

to form a mixture II comprising the compounds IIa(1) and IIb(1):

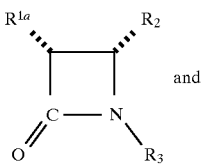

(IIa(1))

and

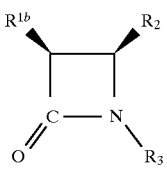

(IIb(1))

27. The method of claim 26, wherein, in said mixture II comprising IIa(1) and IIb(1):

$R^{1a}$ or $R^{1b}$ is alkanoyloxy;

$R^2$ is furyl or thienyl; and $R^3$ is hydrogen, phenyl or substituted phenyl.

28. The method of claim 27, wherein said mixture I comprises (±)-cis-3-hydroxy-4-(2'-furanyl)azetidin-2-one, said mixture II comprises (+)-cis-hydroxy-4-(2'-furanyl)azetidin-2-one and (−)-cis-3-acetoxy-4-(2'-furanyl)azetidin-2-one, and said compound of the formula III is isopropenyl acetate.

29. The method of claim 25, wherein said enzyme is immobilized on a support.

30. The method of claim 25, wherein, further, the non-enantiomeric compounds IIa and IIb of said mixture II obtained are separated by a separation step.

31. The method of claim 30, wherein said separation step is an extraction, distillation, crystallization or column chromatography step.

32. The method of claim 25, comprising the further step of preparing a taxane bearing a C-13 sidechain, wherein said sidechain is formed using at least one of the non-enantiomeric compounds IIa or IIb of said mixture II.

* * * * *